US009339512B2

(12) United States Patent
Widdowson et al.

(10) Patent No.: US 9,339,512 B2
(45) Date of Patent: May 17, 2016

(54) METHOD FOR VECTOR DELIVERY (71) Applicant: Oxford BioMedica (UK) Ltd., Oxford (GB)

(72) Inventors: Peter Widdowson, Oxford (GB); Scott Ralph, Oxford (GB); Kyriacos A. Mitrophanous, Oxford (GB)

(73) Assignee: Oxford BioMedica (UK) Limited, Oxford (GB)

( * ) Notice: Subject to any disclaimer, the term of this patent is extended or adjusted under 35 U.S.C. 154(b) by 0 days.

(21) Appl. No.: 13/893,920

(22) Filed: May 14, 2013

(65) Prior Publication Data

US 2013/0281975 A1 Oct. 24, 2013

Related U.S. Application Data (62) Division of application No. 13/117,451, filed on May 27, 2011, now abandoned.

(30) Foreign Application Priority Data

| May 28, 2010 | (GB) | ................................... | 1009052.0 |
| Jan. 12, 2011 | (GB) | ................................... | 1100502.2 |
| Apr. 28, 2011 | (GB) | ................................... | 1107184.2 |

(51) Int. Cl.
| *A61K 31/70* | (2006.01) |
| *C12N 15/63* | (2006.01) |
| *A61M 31/00* | (2006.01) |
| *A61K 31/711* | (2006.01) |
| *C12N 15/86* | (2006.01) |
| *A61M 5/178* | (2006.01) |
| *A61K 48/00* | (2006.01) |

(52) U.S. Cl.
CPC ............ *A61K 31/711* (2013.01); *A61K 48/0075* (2013.01); *A61K 48/0083* (2013.01); *C12N 15/86* (2013.01); *A61K 48/005* (2013.01); *A61M 5/178* (2013.01); *C12N 2740/15043* (2013.01)

(58) Field of Classification Search
CPC ............ A61K 48/005; A61K 48/0075; A61K 48/0083; C12N 15/86; C12N 2740/15043; A61M 5/178
USPC ........................ 514/44 R; 435/320.1; 604/506
See application file for complete search history.

(56) References Cited

U.S. PATENT DOCUMENTS

| 2004/0202642 | A1* | 10/2004 | Arbischer et al. |
| 2007/0025970 | A1* | 2/2007 | Kingsman et al. |
| 2009/0036393 | A1* | 2/2009 | Kang |
| 2010/0081707 | A1* | 4/2010 | Ali et al. |
| 2010/0324127 | A1* | 12/2010 | Kay |
| 2011/0214195 | A1* | 9/2011 | Eckel et al. |
| 2011/0269826 | A1* | 11/2011 | Kingsman et al. |
| 2013/0331441 | A1* | 12/2013 | Deisseroth et al. |

OTHER PUBLICATIONS

Huszthy, Peter C., Remission of Invasive, Cancer Stem-Like Glioblastoma Xenografts Using Lentiviral Vector-Mediated Suicide Gene Therapy, Jul. 2009, PLoS ONE 4(7)e6314:1-13.

* cited by examiner

*Primary Examiner* — Shin Lin Chen
(74) *Attorney, Agent, or Firm* — Grimes & Yvon LLP (57) ABSTRACT

Provided is a lentiviral vector for delivery to the brain for use in treating a neurological condition, wherein the lentiviral vector is delivered directly to the brain by delivering the lentiviral vector via six or fewer tracts per hemisphere, at a single deposit point per tract.

13 Claims, 3 Drawing Sheets

METHOD FOR VECTOR DELIVERY

CROSS REFERENCE TO RELATED APPLICATIONS

This application is a divisional application of U.S. application Ser. No. 13/117,451, filed on May 27, 2011, currently pending. This application claims the benefit of priority to Great Britain applications 1009052.0, filed on May 28, 2010; 1100502.2, filed on Jan. 12, 2011; and 1107184.2, filed on Apr. 28, 2011. The foregoing applications are hereby incorporated by reference in their entireties.

FIELD OF THE INVENTION

The present invention relates to a lentiviral vector for delivery to the brain for use in treating a neurological condition. The lentiviral vector is delivered directly to the brain by continuous infusion using a narrow bore delivery device with a reduced number of deposit points compared to previous methods.

BACKGROUND TO THE INVENTION

Virus-based approaches are known to treat various neurological diseases, through the introduction of therapeutic genes to transduce neuronal and/or support cells. For example, a multicistronic lentiviral vector product, ProSavin®, has been developed to treat Parkinson's disease. ProSavin® mediates intrastriatal dopamine production by transduction into non-dopamine cells the genes for aromatic L-amino acid decarboxylase, tyrosine hydroxylase, and GTP cyclohydrolase I (Azzouz et at (2002) J Neurosci. 22: 10302-10312).

Previous methods of lentiviral vector delivery have introduced the vectors to specific regions within the brain through multiple small volume deposits at a low discontinuous flow rate to ensure sufficient transduction of target cells over a wide area (Azzouz et at (2002) J Neurosci 22: 10302-10312). For example, ProSavin® is administered using multiple tracts (up to 5 per hemisphere) using a step-wise delivery method which involves multiple deposits of the vector along each tract (Jarraya et at (2009) Sci Transl Med 14: 1(2) 2-4).

Such an approach requires complex pre-surgical planning to determine the positioning of the cannula tracts and time-consuming surgery, with an increased risk of bleeding and other surgical complications associated with the use of multiple cannula tracts to introduce the vector.

There is thus a need for improved delivery methods for such lentiviral vectors.

There are reports of using convection-enhanced delivery (CED) as an efficient method of delivering therapeutic agents, including maghemite nanoparticles, liposomes and small viral vectors, such as adeno-associciated virus vectors (AAV), into the brain (Lieberman et at (1985) J. Neurosurg. 82:1021-1029; Bankiewicz et al (2000) Exp. Neurol. 164:2-14; Cunningham et al (2000) Cell Transplant 9:585-594; Nguyen et al (2001) Neuroreport 12:1961-1964; Mamot et al (2004) J Neurooncol. 68:1-9; Hadaczek et al (2006) Hum. Gene Ther 17:291-302 and Perlstein et al (2008) Neuro-Oncol 10:153-161). Using a pressurised infusate, the distribution of particles and macromolecules through the perivascular space has been reported to be enhanced above that achieved by diffusion alone (Chen et al (2004) J. Neurosurg. 101:314-322 and Hadaczek et al (2009) Hum. Gene Ther 20:229-237).

CED uses a pressure gradient established at the tip of an infusion catheter that initially creates bulk flow that "pushes" the therapeutic agent through the space between brain cells.

Although there are reports of successful use of CED to deliver small AAVs (Bankiewicz et al (2000) Exp. Neurol. 164:2-14; Cunningham et al (2000) Cell Transplant 9:585-594; and Hadaczek et al (2009) Hum. Gene Ther 20:229-237) these findings have little impact on the delivery of lentiviral vectors, because the intracellular space in the brain has been calculated as being between 38 and 64 nm (Thorne and Nicholson (2006) PNAS 104; 5567-5572), whereas the typical diameter of lentiviruses is around 100 nm, typically around four-fold larger than AAV vectors (Fields Virology Fifth Edition (2007) Eds. Knipe and Howley. Lippincott Williams and Wilkins). AAV vectors are non-enveloped viruses with a diameter of around 18-26 nm and are considerably smaller than the calculated intracellular space.

Consideration to the cellular tropism (Davidson et al (2000) Proc. Natl. Acad. Sci. USA, Vol. 97, PP. 3428-3432; Azzouz et al (2002) J Neurosci 22:10302-10312 and Eschemacher et al (2004) Exp Med 90:61-69) is an important factor when changing vector delivery, as neuronal or other cellular targets may be significantly compromised when vectors are delivered in an accelerated fashion. Moreover, the relative immunological response to central vector administration may also be altered when modifying the methodology for surgical administration into specific brain regions.

DESCRIPTION OF THE FIGURES

The data illustrate that administration of vector using a single infusion through a 28-gauge fused silica cannula at a constant flow rate of either 1 or 3 μL/min mediates improved distribution of vector in the putamen compared to the 5 tract delivery method using a 23-gauge needle and syringe. The higher flow rate of 3 μL/min demonstrated a greater volume of vector distribution with the single infusion than the slower rate. Vector delivery using a single infusion with the 23-gauge needle and syringe resulted in a lower volume of vector distribution than both of the methods described above indicating that the gauge of needle is critical for achieving an improved vector distribution in the brain.

SUMMARY OF ASPECTS OF THE INVENTION

The present inventors have surprisingly found that despite the size of lentiviral vectors relative to the extracellular space, it is possible to modify the multiple-tract discontinuous delivery method described for ProSavin®, increase the volume delivered per tract and the flow rate of infusion for lentiviral vectors which in turn results in a greater volume of vector spread within the brain.

Using a lentiviral vector based on the equine infectious anaemia virus (EIAV), expressing the reporter gene β-galactosidase (EIAV-LacZ), they have shown that a single continuous infusion of this genetically modified lentiviral vector distributes effectively within the putamen of cynomolgus macaques. Although vector spread in the rostro-caudal axis of the putamen was marginally less than using the previously described multiple 5 needle tract approach to manually spread out the vector distribution, vector distribution in the medio-lateral and dorso-ventral axes with the continuous single infusion paradigm was better than the 5-tract multiple deposit approach. Moreover the total volume of vector distribution in the brain was almost 2-fold greater with a single continuous infusion compared with the five-tract multiple deposit method.

Despite the increased volume and increased flow rate of administration, the continuous infusion system produced no overt neuronal damage in the region of vector spread and no evidence of damage to the blood-brain barrier. Animals did not display any signs of major toxicity or overt inflammatory responses and no abnormal clinical signs or motor disturbances were observed. This is surprising given the relatively large size of lentiviral vectors. In addition there was less evidence of backflow along the outer surface of the infusion cannula, which had previously been observed with the 23-gauge needle using the 5-tract approach.

This shows that, contrary to expectations in view of their large size, rather than requiring a slow, discontinuous (multiple deposit) infusion of small volumes, large volumes of lentiviral vectors can be "pushed" through the neuronal matrix between cells using fluid convection without causing obvious signs of tissue damage and resulting in superior vector distribution within the target area.

This results in a reduction in the number of tracts required to deliver a given volume of infusate. Thus the increased flow-rate and increased volumes that can be delivered reduces both surgery time and the risks associated with placement of many cannula sites, as well as allowing the delivery of higher doses of lentiviral vector.

It was also found that a narrow gauge cannula resulted in a better volume of vector distribution than a wide bore cannula. It is thought that this is due to reduced back-flow with the narrow gauge cannula and an increase in pressure from the more narrow cannula enhancing the vector distribution. Backflow may be a key problem when delivering a therapeutic under pressure, because if backflow occurs, a significant amount of vector could be lost up the cannula tract and would not be available for delivery to the target area.

Thus, in a first aspect, the present invention provides a lentiviral vector for delivery to the brain for use in treating a neurological condition, wherein a composition comprising the lentiviral vector is delivered directly to the brain by continuous infusion using a cannula and wherein between 10-600 μL of the vector composition is delivered per tract at a flow rate of at least 2 μL/min.

The cannula may be of sufficiently narrow bore to prevent substantial backflow of the vector composition.

The flow rate may be constant or increasing during infusion of the lentiviral vector.

The vector may be an equine infectious anaemia virus (EIAV) vector, for example an EIAV vector which comprises nucleotide sequences encoding Tyrosine Hydroxylase, GTP-cyclohydrolase I and Aromatic Amino Acid Dopa Decarboxylase.

The lentiviral vector may be delivered via a single cannula tract per hemisphere.

The infusion may have a volume of about 50 μL.

The flow rate at which the vector is delivered may be between 2-6 μL/min, for example about 3 μL/min.

The lentiviral vector may be delivered using a cannula with a bore equivalent to or narrower than 28 gauge.

The lentiviral vector may be for treating Parkinson's disease.

In a second aspect, the present invention provides a method for treating a neurological disorder in a subject which comprises the step of administrating a lentiviral vector as defined in any preceding claim to the subject, in which method a composition comprising the lentiviral vector is delivered directly to the brain by continuous infusion using a cannula and wherein between 10-600 μL of the vector composition is delivered per tract at a flow rate of at least 2 μL/min.

In a third aspect there is provided a method for improving the distribution volume of a lentiviral vector in the putamen when administered directly to the brain of a subject, by continuous infusion using a cannula, wherein between 10-600 μL of the vector composition is delivered per tract at a flow rate of at least 2 μL/min.

In a fourth aspect there is provided a kit for delivering a lentiviral vector according to the first aspect of the invention directly to the brain of the subject, which comprises one or more cannulas.

The cannulas may be pre-filled with the lentiviral vector composition at a volume of between 10 and 600 μL.

The kit may comprise one or more cannulas for delivery of the vector, wherein the cannula(s) is/are 28 gauge or narrower.

DETAILED DESCRIPTION

The present invention relates to a lentiviral vector for delivery to the brain.

Lentiviral Vectors

The lentiviral vector according to the present invention may be derived from or may be derivable from any suitable lentivirus. A recombinant lentiviral particle is capable of transducing a target cell with a nucleotide of interest (NOI). Once within the cell the RNA genome from the vector particle is reverse transcribed into DNA and integrated into the genome of the target cell.

Lentiviral vectors are part of a larger group of retroviral vectors. A detailed list of lentiviruses may be found in Coffin et al. (1997) "Retroviruses" Cold Spring Harbor Laboratory Press Eds: J M Coffin, S M Hughes, HE Varmus pp 758-763). In brief, lentiviruses can be divided into primate and non-primate groups. Examples of primate lentiviruses include but are not limited to: the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

Lentiviruses differ from other members of the retrovirus family in that lentiviruses have the capability to infect both dividing and non-dividing cells (Lewis et al (1992) EMBO J 11(8):3053-3058) and Lewis and Emerman (1994) J Virol 68 (1):510-516). In contrast, other retroviruses—such as MLV—are unable to infect non-dividing or slowly dividing cells such as those that make up, for example, muscle, brain, lung and liver tissue.

A lentiviral vector, as used herein, is a vector which comprises at least one component part derivable from a lentivirus. Preferably, that component part is involved in the biological mechanisms by which the vector infects cells, expresses genes or is replicated.

The basic structure of retrovirus and lentivirus genomes share many common features such as a 5' LTR and a 3' LTR, between or within which are located a packaging signal to enable the genome to be packaged, a primer binding site, integration sites to enable integration into a host cell genome and gag, pol and env genes encoding the packaging components—these are polypeptides required for the assembly of viral particles. Lentiviruses have additional features, such as rev and RRE sequences in HIV, which enable the efficient export of RNA transcripts of the integrated provirus from the nucleus to the cytoplasm of an infected target cell.

In the provirus, the viral genes are flanked at both ends by regions called long terminal repeats (LTRs). The LTRs are responsible for proviral integration, and transcription. LTRs also serve as enhancer-promoter sequences and can control the expression of the viral genes.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different viruses.

In a defective lentiviral vector genome gag, pol and env may be absent or not functional. The R regions at both ends of the RNA are repeated sequences. U5 and U3 represent unique sequences at the 5' and 3' ends of the RNA genome respectively.

In a typical lentiviral vector of the present invention, at least part of one or more protein coding regions essential for replication may be removed from the virus. This makes the viral vector replication-defective. Portions of the viral genome may also be replaced by an NOI in order to generate a vector comprising an NOI which is capable of transducing a target non-dividing host cell and/or integrating its genome into a host genome.

In one embodiment the lentiviral vectors are non-integrating vectors as described in WO 2007/071994.

In a further embodiment the vectors have the ability to deliver a sequence which is devoid of or lacking viral RNA. In a further embodiment a heterologous binding domain (heterologous to gag) located on the RNA to be delivered and a cognate binding domain on gag or pol can be used to ensure packaging of the RNA to be delivered. Both of these vectors are described in WO 2007/072056.

The lentiviral vector may be a "non-primate" vector, i.e., derived from a virus which does not primarily infect primates, especially humans.

The examples of non-primate lentivirus may be any member of the family of lentiviridae which does not naturally infect a primate and may include a feline immunodeficiency virus (FIV), a bovine immunodeficiency virus (BIV), a caprine arthritis encephalitis virus (CAEV), a Maedi visna virus (MVV) or an equine infectious anaemia virus (EIAV).

In a particularly preferred embodiment the viral vector is derived from EIAV. EIAV has the simplest genomic structure of the lentiviruses and is particularly preferred for use in the present invention. In addition to the gag, pol and env genes EIAV encodes three other genes: tat, rev, and S2. Tat acts as a transcriptional activator of the viral LTR (Derse and Newbold (1993) Virology 194(2):530-536 and Maury et al (1994) Virology 200(2):632-642) and Rev regulates and coordinates the expression of viral genes through rev-response elements (RRE) (Martarano et al. (1994) J Virol 68(5):3102-3111). The mechanisms of action of these two proteins are thought to be broadly similar to the analogous mechanisms in the primate viruses (Martarano et al. (1994) J Virol 68(5):3102-3111). The function of S2 is unknown. In addition, an EIAV protein, Ttm, has been identified that is encoded by the first exon of tat spliced to the env coding sequence at the start of the transmembrane protein.

Preferred vectors of the present invention are recombinant lentiviral vectors.

The term "recombinant lentiviral vector" refers to a vector with sufficient lentiviral genetic information to allow packaging of an RNA genome, in the presence of packaging components, into a viral particle capable of infecting a target cell. Infection of the target cell may include reverse transcription and integration into the target cell genome. The recombinant lentiviral vector carries non-viral coding sequences which are to be delivered by the vector to the target cell. A recombinant lentiviral vector is incapable of independent replication to produce infectious lentiviral particles within the final target cell. Usually the recombinant lentiviral vector lacks a functional gag-pol and/or env gene and/or other genes essential for replication. The vector of the present invention may be configured as a split-intron vector. A split intron vector is described in PCT patent application WO 99/15683.

Preferably the recombinant lentiviral vector of the present invention has a minimal viral genome.

As used herein, the term "minimal viral genome" means that the viral vector has been manipulated so as to remove the non-essential elements and to retain the essential elements in order to provide the required functionality to infect, transduce and deliver a nucleotide sequence of interest to a target host cell. Further details of this strategy can be found in our WO 98/17815.

In one embodiment of the present invention, the vector is a self-inactivating vector.

By way of example, self-inactivating retroviral vectors have been constructed by deleting the transcriptional enhancers or the enhancers and promoter in the U3 region of the 3' LTR. After a round of vector reverse transcription and integration, these changes are copied into both the 5' and the 3' LTRs producing a transcriptionally inactive provirus (Yu et al (1986) Proc. Natl. Acad. Sci. 83:3194-3198; Dougherty and Temin et al (1987) Proc. Natl. Acad. Sci. 84:1197-1201; Hawley (1987) Proc. Natl. Acad. Sci. 84:2406-2410 and Yee et al (1987) Proc. Natl. Acad. Sci. 91:9564-9568). However, any promoter(s) internal to the LTRs in such vectors will still be transcriptionally active. This strategy has been employed to eliminate effects of the enhancers and promoters in the viral LTRs on transcription from internally placed genes. Such effects include increased transcription (Jolly et al (1983) Nucleic Acids Res. 11:1855-1872) or suppression of transcription (Emerman and Temin (1984) Cell 39:449-467). This strategy can also be used to eliminate downstream transcription from the 3' LTR into genomic DNA (Herman and Coffin (1987) Science 236:845-848). This is of particular concern in human gene therapy where it is of critical importance to prevent the adventitious activation of an endogenous oncogene.

However, the plasmid vector used to produce the viral genome within a host cell/packaging cell will also include transcriptional regulatory control sequences operably linked to the lentiviral genome to direct transcription of the genome in a host cell/packaging cell. These regulatory sequences may be the natural sequences associated with the transcribed lentiviral sequence, i.e. the 5' U3 region, or they may be a heterologous promoter such as another viral promoter, for example the CMV promoter. Some lentiviral genomes require additional sequences for efficient virus production. For example, in the case of HIV, rev and RRE sequence are preferably included. However the requirement for rev and RRE may be reduced or eliminated by codon optimisation. Further details of this strategy can be found in WO 01/79518. Alternative sequences which perform the same function as the rev/RRE system are also known. For example, a functional analogue of the rev/RRE system is found in the Mason Pfizer monkey virus. This is known as the constitutive transport element (CTE) and comprises an RRE-type sequence in the genome which is believed to interact with a factor in the infected cell. The cellular factor can be thought of as a rev analogue. Thus, CTE may be used as an alternative to the rev/RRE system. Any other functional equivalents which are known or become available may be relevant to the invention. For example, it is also known that the Rex protein of HTLV-I can functionally replace the Rev protein of HIV-1. It is also known that Rev and Rex have similar effects to IRE-BP.

In a particularly preferred embodiment, the lentiviral vector according to the present invention consists of a self-inactivating minimal lentiviral vector, derived from Equine Infectious Anaemia Virus (EIAV), preferably encoding three enzymes that are involved in the dopamine synthetic pathway. The proteins encoded by such a vector may comprise a truncated form of the human tyrosine hydroxylase (TH*) gene (which lacks the N-terminal 160 amino acids involved in feedback regulation of TH), the human aromatic L-amino-acid decarboxylase (AADC), and the human GTP-cyclohydrolase 1 (GTP-CH1) gene. The vector may be produced by the transient transfection of cells (e.g. HEK293T cells) with three plasmids, encoding for: (1) the recombinant EIAV Pro-Savin® (Oxford BioMedica plc, Oxford UK) vector genome (pONYK1-ORT, WO 02/29065 and Farley et al (2007) J. Gen. Med. 9:345-356); (2) the synthetic EIAV gag/pol expression vector (pESGPK, WO 01/79518 and WO 05/29065) and (3) the VSV-G envelope expression vector (pHGK)

Packaging Sequence

As utilised within the context of the present invention the term "packaging signal" which is referred to interchangeably as "packaging sequence" or "psi" is used in reference to the non-coding, cis-acting sequence required for encapsidation of lentiviral RNA strands during viral particle formation. In HIV-1, this sequence has been mapped to loci extending from upstream of the major splice donor site (SD) to at least the gag start codon.

As used herein, the term "extended packaging signal" or "extended packaging sequence" refers to the use of sequences around the psi sequence with further extension into the gag gene. The inclusion of these additional packaging sequences may increase the efficiency of insertion of vector RNA into viral particles.

Pseudotyping

Preferably, the lentiviral vector according to the present invention has been pseudotyped. In this regard, pseudotyping can confer one or more advantages. For example, with the lentiviral vectors, the env gene product of the HIV based vectors would restrict these vectors to infecting only cells that express a protein called CD4. But if the env gene in these vectors has been substituted with env sequences from other RNA viruses, then they may have a broader infectious spectrum (Verma and Somia (1997) Nature 389(6648):239-242). By way of examples, Miller et al. pseudotyped an MoMLV vector with the envelope from the amphotropic retrovirus 4070A (Mol. Cell. Biol. 5:431-437) other workers have pseudotyped an HIV based lentiviral vector with the glycoprotein from VSV (Verma and Somia (1997) Nature 389 (6648):239-242).

In another alternative, the Env protein may be a modified Env protein such as a mutant or engineered Env protein. Modifications may be made or selected to introduce targeting ability or to reduce toxicity or for another purpose (Marin et al (1996) J Virol 70(5):2957-2962; Nilson et al (1996) Gene Ther 3(4):280-286; and Fielding et al (1998) Blood 91(5): 1802-1809 and references cited therein).

The vector may be pseudotyped, for example with a gene encoding at least part of the rabies G protein or the VSV-G protein.

VSV-G:

The envelope glycoprotein (G) of Vesicular stomatitis virus (VSV), a rhabdovirus, is an envelope protein that has been shown to be capable of pseudotyping certain retroviruses including lentiviruses.

Its ability to pseudotype MoMLV-based retroviral vectors in the absence of any retroviral envelope proteins was first shown by Emi et al. (1991) J. Virol. 65:1202-1207). WO 94/294440 teaches that retroviral vectors may be successfully pseudotyped with VSV-G. These pseudotyped VSV-G vectors may be used to transduce a wide range of mammalian cells. More recently, Abe et al. (1998) J. Virol 72(8): 6356-6361 teach that non-infectious retroviral particles can be made infectious by the addition of VSV-G.

Burns et al (1993) Proc. Natl. Acad. Sci. USA 90:8033-8037) successfully pseudotyped the retrovirus MLV with VSV-G and this resulted in a vector having an altered host range compared to MLV in its native form. VSV-G pseudotyped vectors have been shown to infect not only mammalian cells, but also cell lines derived from fish, reptiles and insects (Burns et al (1993) Proc. Natl. Acad. Sci. USA 90:8033-8037). They have also been shown to be more efficient than traditional amphotropic envelopes for a variety of cell lines (Yee et al. (1994) Proc. Natl. Acad. Sci. USA 91:9564-9568 and Emi et al. (1991) J. Virol. 65:1202-1207). VSV-G protein can also be used to pseudotype certain lentiviruses and retroviruses because its cytoplasmic tail is capable of interacting with the retroviral cores.

The provision of a non-lentiviral pseudotyping envelope such as VSV-G protein gives the advantage that vector particles can be concentrated to a high titre without loss of infectivity (Akkina et al (1996) J. Virol. 70:2581-2585). Lentivirus and retrovirus envelope proteins are apparently unable to withstand the shearing forces during ultracentrifugation, probably because they consist of two non-covalently linked subunits. The interaction between the subunits may be disrupted by the centrifugation. In comparison the VSV glycoprotein is composed of a single unit. VSV-G protein pseudotyping can therefore offer potential advantages.

WO 00/52188 describes the generation of pseudotyped retroviral and lentiviral vectors, from stable producer cell lines, having vesicular stomatitis virus-G protein (VSV-G) as the membrane-associated viral envelope protein, and provides a gene sequence for the VSV-G protein.

Ross River Virus

The Ross River viral envelope has been used to pseudotype a nonprimate lentiviral vector (FIV) and following systemic administration predominantly transduced the liver (Kang et al (2002) J Virol 76(18):9378-9388.). Efficiency was reported to be 20-fold greater than obtained with VSV-G pseudotyped vector, and caused less cytotoxicity as measured by serum levels of liver enzymes suggestive of hepatotoxicity.

Ross River Virus (RRV) is an alphavirus spread by mosquitoes which is endemic and epidemic in tropical and temperate regions of Australia. Antibody rates in normal populations in the temperate coastal zone tend to be low (6% to 15%) although sero-prevalence reaches 27 to 37% in the plains of the Murray Valley River system. In 1979 to 1980 Ross River Virus became epidemic in the Pacific Islands. The disease is not contagious between humans and is never fatal, the first symptom being joint pain with fatigue and lethargy in about half of patients (Fields Virology Fifth Edition (2007) Eds. Knipe and Howley. Lippincott Williams and Wilkins)

Baculovirus GP64

The baculovirus GP64 protein has been shown to be an attractive alternative to VSV-G for viral vectors used in the large-scale production of high-titre virus required for clinical and commercial applications (Kumar M, Bradow B P, Zimmerberg J (2003) Hum. Gene Ther. 14(1):67-77). Compared with VSV-G-pseudotyped vectors, GP64-pseudotyped vectors have a similar broad tropism and similar native titres. Because, GP64 expression does not kill cells, 293T-based cell lines constitutively expressing GP64 can be generated.

Rabies G

In the present invention the vector may be pseudotyped with at least a part of a rabies G protein or a mutant, variant, homologue or fragment thereof.

Teachings on the rabies G protein, as well as mutants thereof, may be found in WO 99/61639 and well as Rose et al (1982) J. Virol. 43:361-364, Hanham et al (1993) J. Virol. 67:530-542; Tuffereau et al (1998) J. Virol. 72:1085-1091, Kucera et al (1985) J. Virol. 55:158-162; Dietzschold et al (1983) PNAS 80:70-74; Seif et al (1985) J. Virol. 53:926-934; Coulon et al (1998) J. Virol. 72:273-278; Tuffereau et al (1998) J. Virol. 72:1085-10910; Burger et al (1991) J. Gen. Virol. 72:359-367; Gaudin et al (1995) J. Virol. 69:5528-5534; Benmansour et al (1991) J. Virol. 65:4198-4203; Luo et al (1998) Microbiol. Immunol. 42:187-193, Coll (1997) Arch. Virol. 142:2089-2097; Luo et al (1997) Virus Res. 51:35-41; Luo et al (1998) Microbiol. Immunol. 42:187-193; Coll (1995) Arch. Virol. 140:827-851; Tuchiya et al (1992) Virus Res. 25:1-13; Morimoto et al (1992) Virology 189:203-216; Gaudin et al (1992) Virology 187:627-632; Whitt et al (1991) Virology 185:681-688; Dietzschold et al (1978) J. Gen. Virol. 40:131-139; Dietzschold et al (1978) Dev. Biol. Stand. 40:45-55; Dietzschold et al (1977) J. Virol. 23:286-293 and Otvos et al (1994) Biochim. Biophys. Acta 1224:68-76. A rabies G protein is also described in EP 0445625.

Alternative Envelopes

Other envelopes which can be used to pseudotype lentiviral vectors include Mokola, Ebola, 4070A and LCMV (lymphocytic choriomeningitis virus).

Retroviral and lentiviral vectors have been proposed as a delivery system for the transfer of a nucleotide of interest (NOI) in vivo to one or more sites of interest.

The expression products encoded by the NOIs may be proteins which are secreted from the cell. Alternatively the NOI expression products are not secreted and are active within the cell.

The or each NOI may be prophylactically, therapeutically and/or diagnostically relevant to a neurological disorder. Suitable NOIs include, but are not limited to: sequences encoding enzymes, cytokines, chemokines, hormones, antibodies, anti-oxidant molecules, engineered immunoglobulin-like molecules, a single chain antibody, fusion proteins, immune co-stimulatory molecules, immunomodulatory molecules, anti-sense RNA, microRNA, shRNA, siRNA, ribozymes, a transdomain negative mutant of a target protein, a toxin, a conditional toxin, an antigen, a tumour suppresser protein and growth factors, membrane proteins, vasoactive proteins and peptides, anti-viral proteins and ribozymes, and derivatives thereof (such as with an associated reporter group). The NOIs may also encode pro-drug activating enzymes.

In the present invention, the NOI can be, for example, a synthetic RNA/DNA sequence, a recombinant RNA/DNA sequence (i.e. prepared by use of recombinant DNA techniques), a cDNA sequence or a partial genomic DNA sequence.

The NOI may be useful in the treatment of a neurodegenerative disorder, for example Parkinson's disease.

The NOI may encode an enzyme or enzymes involved in dopamine synthesis or storage. For example, the enzyme may be one or more of the following: Tyrosine Hydroxylase (TH), GTP-cyclohydrolase I (GTP-CH1) and/or Aromatic Amino Acid Dopa Decarboxylase (AADC). The sequences of all three genes are available: Accession Nos. X05290, U19523 and M76180 respectively.

Alternatively the NOI may encode the vesicular monoamine transporter 2 (VMAT2, Accession number L23205.1). The viral genome may comprise an NOI encoding AADC and an NOI encoding VMAT 2. Such a genome may be used in the treatment of Parkinson's disease, in particular in conjunction with peripheral administration of L-DOPA.

Alternatively the NOI may encode a growth factor capable of blocking or inhibiting degeneration in the nigrostriatal system or which prevents TH-positive neurones from dying, or which stimulates regeneration and functional recovery. For example the NOI may encode glial cell-line derived neurotrophic factor (GDNF), brain-derived neurotrophic factor (BDNF), nerve growth factor (NGF), persephin growth factor, artemin growth factor, or neurturin growth factor, cilliary neurotrophic factor (CNTF), neurotrophin-3 (NT-3), neurotrophin-4 (NT-4), pantropic neurotrophin, acidic fibroblast growth factor (aFGF), basic fibroblast growth factor (bFGF), interleukin-1 beta (IL-1β), tumor necrosis factor alpha (TNF-α), insulin growth factor-2, VEGF-A, VEGF-B, VEGF-C/VEGF-2, VEGF-D, VEGF-E, PDGF-A, PDGF-B, hetero- and homo-dimers of PDFG-A and PDFG-B and other related or unrelated neurotrophic factors. The lentiviral vector may comprise one or more of these NOIs encoding neurotrophic factors.

The NOI may also encode an anti-angiogenic protein or anti-angiogenic proteins selected from the group consisting of angiostatin, endostatin; platelet factor 4, pigment epithelium derived factor (PEDF), restin, interferon-alpha, interferon-inducible protein, gro-beta and tubedown-1, Interleukin(IL)-1, IL-12, retinoic acid, anti-VEGF antibodies, aptamers, antisense oligos, siRNA, thrombospondin, VEGF receptor proteins such as those described in U.S. Pat. No. 5,952,199 and U.S. Pat. No. 6,100,071, and anti-VEGF receptor antibodies.

The NOI may encode all or part of the protein of interest ("POI"), or a mutant, homologue or variant thereof. For example, the NOI may encode a fragment of the POI which is capable of functioning in vivo in an analogous manner to the wild-type protein.

One of the NOIs may comprise a truncated form of the TH gene, lacking the regulatory domain. Such an NOI avoids feed-back inhibition by dopamine which may limit expression of the full-length enzyme.

The term "mutant" includes POIs which include one or more amino acid variations from the wild-type sequence. For example, a mutant may comprise one or more amino acid additions, deletions or substitutions. A mutant may arise naturally, or may be created artificially (for example by site-directed mutagenesis).

Here, the term "homologue" means an entity having a certain homology with the NOI, or which encodes a protein having a degree of homology with the POI. Here, the term "homology" can be equated with "identity".

In the present context, a homologous sequence may be at least 75, 85 or 90% identical, or at least 95 or 98% identical to the subject sequence at the amino acid or nucleotide level. Typically, the homologues will comprise or encode the same active sites etc. as the subject sequence.

A number of NOIs may be used in combination. If the lentiviral vector comprises two or more NOIs, in order for both of the NOIs to be expressed, there may be two or more transcription units within the vector genome, one for each NOI. However, it is clear from the literature that retroviral vectors achieve the highest titres and most potent gene expression properties if they are kept genetically simple, so it is preferable to use one or more internal ribosome entry site(s) (IRES) to initiate translation of the second (and subsequent) coding sequence(s) in a poly-cistronic message (Adam et al 1991 J. Virol. 65:4985). An example of such vectors is described in WO 02/29605.

Pharmaceutical Composition

The lentiviral vector of the present invention may be provided in the form of a pharmaceutical composition. The pharmaceutical composition may be used for treating an individual by gene therapy, wherein the composition comprises a therapeutically effective amount of the lentiviral vector.

The viral preparation may concentrated by ultracentrifugation. WO 2009/153563 describes methods for the downstream processing of lentiviral vectors. The resulting pharmaceutical composition may have at least $10^7$ T.U./mL, for example from $10^7$ to $10^9$ T.U./mL, or at least $10^9$ T.U./mL. (The titer is expressed in transducing units per mL (T.U./mL) as titred on a standard D17 of HEK293T cell lines).

The pharmaceutical composition may be used to treat a human or animal, for example a primate animal subject or a companion animal subject.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilising agent(s), and other carrier agents that may aid or increase the viral entry into the target site (such as for example a lipid delivery system).

Diseases

The lentiviral vector used in the present invention is for use in treating a neurological condition. For example, the vector may be useful for the treatment and/or prevention of neurodegenerative diseases.

Diseases which may be treated include, but are not limited to: Parkinson's disease; amyotrophic lateral sclerosis (motor neurone disease); Huntington's disease, and disorders of movement, such as Friedreich's ataxia, cerebellar ataxia, dystonias, repetitive motion disorders, restless leg syndrome, tremor and myoclonus; Alzheimer's disease and Pick's disease; stroke; focal and generalised or idiopathic epilepsy; chronic pain, including paresthesias, back pain, and diabetic neuropathy; brain tumours; chronic fatigue syndrome; Creutzfeldt-Jakob disease (CJD) and variant CJD; leukodystrophies, including Tay-Sachs disease, and Wilson's disease; changes to intracranial pressure; cluster headaches and migraine; multiple sclerosis; chronic eating disorders including Prader-Willi disorder; schizophrenia; affective disorders; mania and sleeping disorders including sleep apnea.

In particular, the present invention is useful in treating and/or preventing Parkinson's disease.

Treatment by gene therapy with vectors capable of delivering, for example, TH, GTP-CH1 and optionally AADC or AADC and VMAT2, is likely to be particularly useful for the late stages of PD patients which do not respond significantly to L-dopa treatment. Treatment using AADC or AADC and VMAT2, in combination with L-dopa administered peripherally may also be useful for late stage PD patients.

Administration

The lentiviral vector used in the present invention is administered to the brain, for example by injection into the caudate putamen.

The vector may be administered via one, two, three, four, five, six or more tracts per hemisphere.

The term cannula as used herein shall include cannulas, catheters, needle or any other suitable device for the delivery of therapeutics directly to the brain. WO 2008/100930, WO 2008/144585 and WO 2009/101397 describe such cannulas which could be used.

In a previously described administration system for a lentiviral vector (Jarraya et al (2009) Sci Transl Med 14: 1(2) 2-4), the vector composition was administered in a discontinuous or "punctate" fashion, by administering an aliquot (4 µL) at the bottom of the tract, withdrawing the needle a little way, then administering a second aliquot (3 µL) and withdrawing the needle a little further, (second time); then administering a third aliquot (3 µL); thus aliquots had been deposited at 3 points along each needle tract delivering a total of 10 µL.

Disadvantages associated with this system include the fact that it is very slow and labour-intensive, and that, as there are 5 needle tracts per hemisphere with 3 administration sites per tract, there are fifteen potential sites for tissue damage and inflammation in each hemisphere. Because of this, it is not possible to increase the dose of vector administered to each hemisphere using this method of vector delivery as it would increase the surgery time significantly.

In the method of the present invention, the vector may be delivered at one deposit point for each tract and larger volumes can be delivered via each tract. In the method of the invention, the vector composition is continuously infused. Continuous administration at a single point overcomes the disadvantages mentioned above in connection with the previous system. Using this method, higher doses of vector can be administered to each hemisphere within a practical surgery time.

The term "continuous infusion" means that infusion of the vector composition does not stop and the needle is not moved during delivery. For a given cannula, the entire volume of vector composition to be delivered is administered at a single deposit point and in one "push".

During continuous infusion, the flow rate of the vector composition may be substantially constant, gradually increased or increased in a stepwise manner.

Delivery "directly to the brain" means that the lentiviral vector is administered directly to brain tissue using an invasive procedure such as injection. The lentiviral vector may be delivered to the putamen, for example the motor putamen.

During delivery the volume of lentiviral vector delivered via each cannula tract may be 10-600 μL, or about 40-200 μL may be delivered per tract. One to six tracts may be used for each hemisphere.

The vector may be delivered using a cannula of sufficiently narrow bore to prevent substantial backflow of the vector composition. For example, the cannula may be of a bore such that less than 20%, 15%, 10% or 5% of the vector composition flows back up the needle during or after delivery.

The vector may be delivered using a cannula having an outlet equal to or narrower in diameter than a 23-gauge needle. The outlet may be about 28-gauge. The device may have an outlet of less than 23-gauge and more than 33-gauge.

The internal diameter of the cannula may be may be less that 0.35, 0.3, 0.35, 0.2 or 0.15 mm.

The present invention also provides a method for improving distribution of a lentiviral vector in the medio-lateral and dorso-ventral axes of the putamen when administered directly to the brain of a subject, by delivering the lentiviral vector using a continuous infusion for each cannula tract.

Adaptation of an existing method in order to improve distribution of the lentiviral vector in the medio-lateral and dorso-ventral axes of the putamen and to allow dose escalation may involve any or all of the following: reduction in the number of deposit point per tract; using continuous infusion of the lentiviral vector composition; creating and/or maintaining a pressure gradient during interstitial infusion; using a higher flow rate; and/or delivering a larger volume.

Typically a lentiviral vector is delivered using a cannula or other injection device which is inserted into the brain tissue in the chosen subject. When delivering ProSavin® for the treatment of Parkinson's disease, the striatum is a suitable area of the brain to target. Other areas would be suitable for the treatment of other neurological disorders. One skilled in the art could readily determine which general area of the CNS would be an appropriate target. Stereotactic maps and positioning devices are available. Positioning may also be conducted by using anatomical maps obtained by CT and/or MR imaging of the subject's brain to help guide the injection device to the chosen target area.

Fluid Convection

In a previously described administration system for a lentiviral vector (Jarraya et al (2009) as above), the vector composition penetrated the brain parenchyma by diffusion. Diffusion depends on the free concentration gradient along with the diffusivity of the agent. Dispersal by diffusion may result in poor penetration, particularly for high molecular weight agents such as lentiviral vectors.

The diffusion of therapeutics within the extracellular space is necessary to enable such therapeutics to access the target tissues such as neuronal and glial cells. Thorne and Nicholson (Thorne and Nicholson (2006) PNAS 104; 5567-5572) have determined that the normal extracellular space is between 38 and 64 nm. They suggest that nanoparticle delivery systems of greater than 100 nm will be too large to transit the normal extracellular space. As stated above lentiviral vectors are viral-based nanoparticle delivery systems with diameters of around 100 nm.

In the method of the invention, the lentiviral vector solution is dispersed by fluid convection. Interstitial infusion is performed using a high flow rate which the inventors have shown to greatly enhance the distribution of the lentiviral vector.

The flow rate may be maintained at a steady state during continuous infusion of the vector, or it may be increased in order to maintain the convection pressure (see below). An increasing pressure gradient may be, for example, steadily increasing or it may follow a ramped procedure characterised by several small step-wise increases of flow rate during the continuous infusion.

Fluid pressure may be maintained, gradually increased or ramped during delivery using systems known in the art, such as a programmable osmotic, infusion or other pump known to one skilled in the art.

The high flow rate is maintained for the entire infusion process, delivering the complete volume of vector (e.g. 10 to 600 μL).

Infusion pressure is a function of flow rate, viscosity of lentiviral vector preparation, and cannula size. The infusion pressure should be selected such that it provides a sufficient pressure gradient to enhance distribution of the lentiviral vector, but insufficient to a) cause significant damage to the tissue surrounding the administration site; and/or b) cause "back-flow" and leakage of the solution out of the cannula tract.

In the method of the present invention, the lentiviral vector may be infused into the brain at a flow rate of at least 1.0 μL/min, 1.5 μL/min, or 2 μL/min, or between 1-2 μL/min, between 1-3 μL/min, between 2-6 μL/min, between 2-4 μL/min or between 2.5-3.5 μL/min. The lentiviral vector may be infused into the brain at a flow rate of about 3 μL/min.

During infusion, the convection pressure (which is the difference between infusion pressure and intracranial pressure) may decrease as the total volume delivered increases. In order to maintain convention pressure, the flow rate may be steadily increased during administration. If such a system is employed, the flow rates mentioned in the preceding paragraph may represent the starting flow rates.

Kit

The present invention also provides a kit for delivering a lentiviral vector directly to the brain of the subject, which comprises one to twelve cannulas. Cannulas may be re-used for multiple tracts for each patient or a new cannula may be used for each tract.

The vector may be delivered for example, using a cannula or catheter or a needle (such as a Hamilton needle). The term cannula as used herein shall include cannulas, catheters, needle or any other suitable device for the delivery of therapeutics directly to the brain. WO 2008/100930, WO 2008/144585 and WO 2009/101397 describe such cannulas which could be used.

The cannula may be pre-filled with the lentiviral vector composition. The cannula may be primed prior to positioning within the brain.

The delivery device may, for example, be a stainless steel 28-gauge Hamilton syringe or a fused silica 28-gauge infusion cannula.

If the kit is for use in a method employing one delivery tract per hemisphere, the cannula may, for example, be capable of delivering between about 40 μL, 100 μL, 150 μL, 200 μL, 300 μL, 400 μL, 500 μL or 600 μL of the lentiviral vector. If the kit is for use in a method employing two delivery tracts per hemisphere, the kit may comprise four cannulas. Alternatively a single cannula may be re-used for each tract, or one cannula may be used to deliver vector to each hemisphere, in which case it would be filled with the lentiviral vector composition and primed before each insertion into the target area.

The cannula may also be pre-connected or adapted for connection to an infusion device such as a pump described above. Alternatively the cannula may be attached to known systems for vector administration, such as a syringe which is controlled by a micropump such as those distributed by World Precision Instruments, or the microinjector system (Kopf, USA). Such a delivery system may be suitable for use with a stereotactic frame.

In a further aspect of the invention the narrow bore delivery devices used in connection with the method the invention may be implanted in a subject, to remain over a substantial period of time extending at least several hours to days or more, thus allowing infusion of vector to take place outside of an operating room. It may be desirable that such devices are sufficiently resilient that they can be secured with a fixation device to prevent movement away from the target without damaging the cannula infusion system. It is also desirable that such devices can be imaged to confirm the location in the brain and to ensure that the catheter has not moved from the target at any point.

Narrow bore delivery devices suitable for use in the present invention may have a sufficiently small diameter at the distal, infusion end, to minimize local tissue trauma, with a very small dead space yet with the strength of a larger catheter to prevent breakage and permit fixation, and with the ability to visualize the catheter by imaging.

As will be known to those skilled in the art, there are a number of narrow bore delivery devices that may be suitable for use in the present invention (for example, see the delivery device described in WO 2007/044023).

The narrow bore infusion device of the invention is optionally attached to the head of the subject. Potential fixation methods include, but are not limited to, fixation to the skull near the burr hole with a metal plate, such as a titanium plate, fixation with a plastic capping system placed within the burr hole, or externalization through the scalp and suturing of the guide catheter to the scalp.

The kit may also comprise instructions for storage and/or use.

The invention will now be further described by way of Examples, which are meant to serve to assist one of ordinary skill in the art in carrying out the invention and are not intended in any way to limit the scope of the invention.

EXAMPLES

Example 1

Figure 1A:
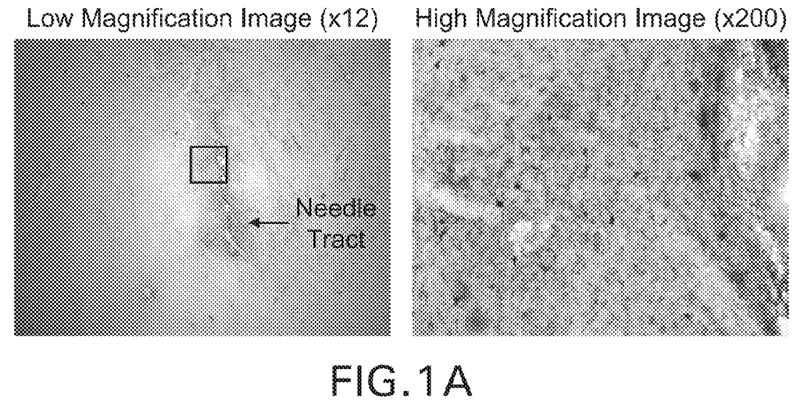
FIGS. 1A-1C show staining for anti-β-galactosidase in non-human primate putamen following administration of 50 μL EIAV-LacZ vector suspension using (A) 5 needle tracts, each delivering 10 μL at 3 points with a 23-gauge Hamilton stainless steel needle (B) a single infusion at 3 μL/min through a 28-gauge fused silica cannula or (C) infusion of 50 μL of TSSM formulation buffer only through a 28-gauge fused silica cannula at 1 μL/min. This figure illustrates the superior medio-lateral and dorso-ventral spread of EIAV vector in the putamen following administration using a single infusion (B) compared to the established method of 5 needle tracts (A) in which vector is more confined to the proximity of the injection tract. The high power images indicate the neuronal morphology of the EIAV transduced cells which is similar with both delivery methods. The TSSM buffer injection provides a negative control for the histological staining.
Figure 1B:
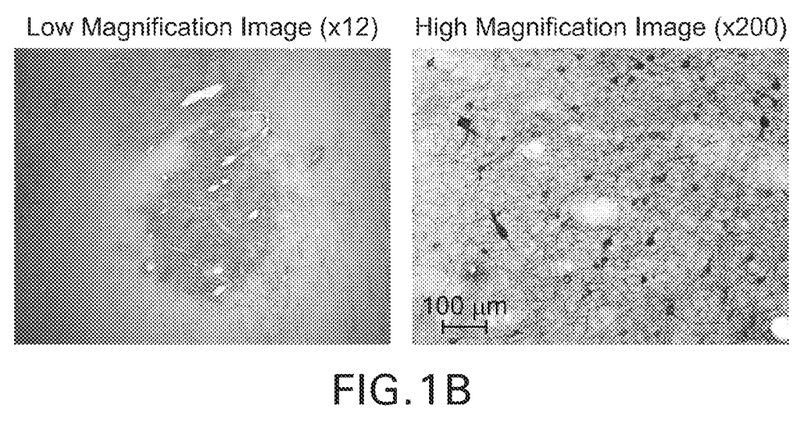
Figure 1C:
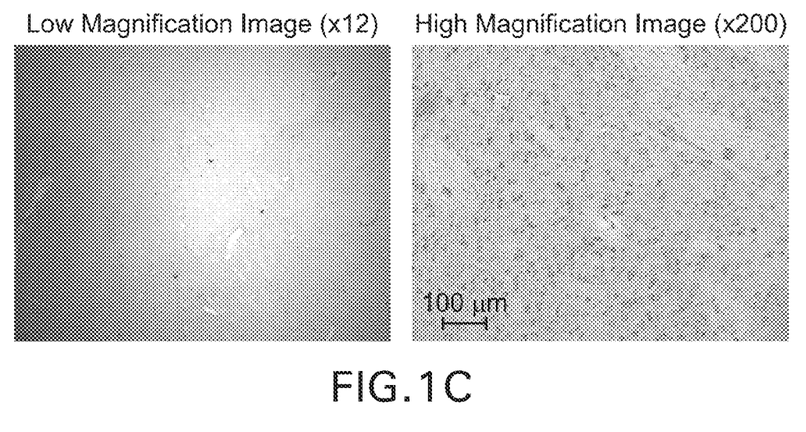
Figure 2:
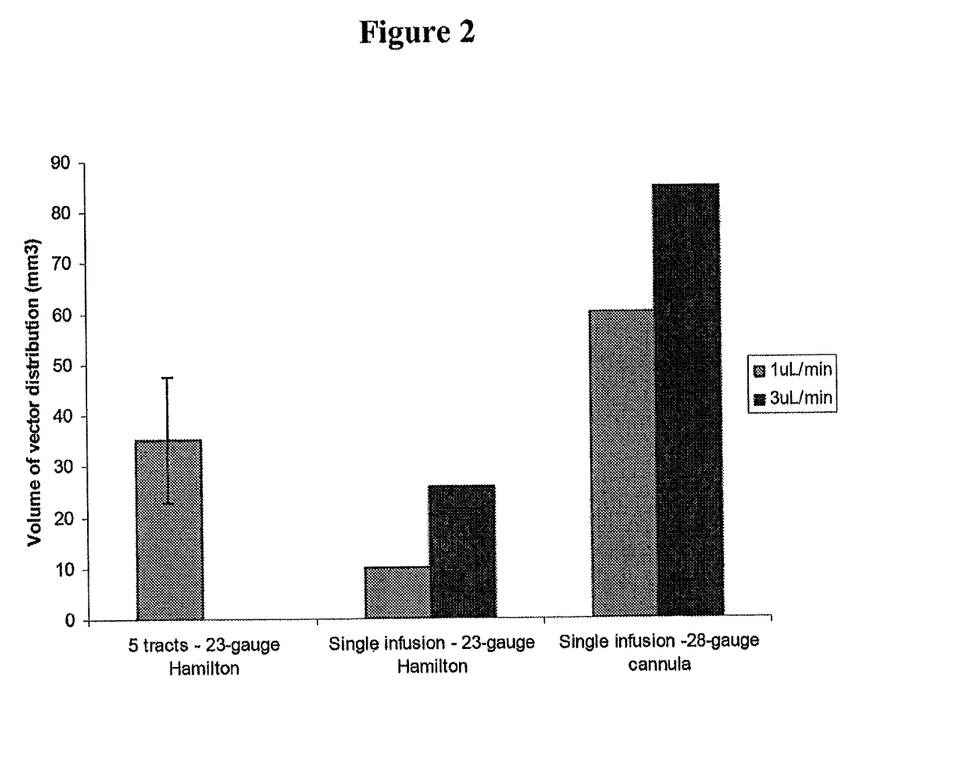
FIG. 2 shows estimation of the volume of vector distribution in non-human primate putamen using stereology methods following administration of 50 μL EIAV-LacZ vector suspension using different delivery methods.
Figure 3:
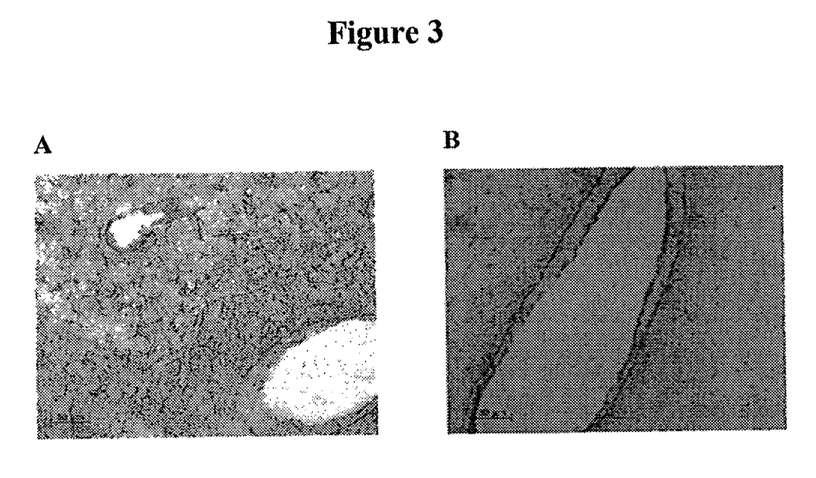
FIGS. 3A-3B show low power photomicrographs showing CD68-positive staining of activated microglia in sections which received 50 μL EIAV-LacZ vector suspension using (A) 5 needle tracts with a 23-gauge Hamilton stainless steel needle or (B) a single infusion through a 28-gauge fused silica cannula. This figure illustrates that for both delivery methods the inflammatory response is local and confined to the area of the needle tract.

Comparing Distribution of a Lentiviral Vector in the Putamen Following a) Conventional Delivery and b) Delivery Using a Single Site and a High Flow-Rate Administration of EIAV-LacZ vector suspension using the previously described technique (50 µL total volume vector administered to the putamen through 5 needle tracts using a Hamilton syringe and 23-gauge needle, each delivering 10 µL per tract (via three deposits) provided a moderate spread of vector in the dorso-ventral axis of the putamen that reached between 40 and 50% the depth of this brain structure (FIG. 1).

Spread of vector in the medio-lateral axis was very much less than with the dorso-ventral axis, with the vector only spreading around 1-2 mm at the greatest point. However, due to the positioning of the five needle tracts along the axis of the putamen, spread of vector along the rostro-caudal axis was around 7.8 mm in both of the two hemispheres that were administered vector by this paradigm.

In contrast, using the method of the present invention (infusing the entire 50 µL of vector suspension at one site in the putamen through the 23-gauge needle with a Hamilton syringe or using a 28-gauge fused silica cannula at either 1 or 3 µL/min) produced improved vector spread in the medio-lateral and dorso-ventral axis compared with the five tract regimen with the greatest degree of spread observed with the 28-gauge cannula at either 1 or 3 µL/min flow rates.

Vector delivery of 50 µL vector using a single tract of delivery with the 28-gauge cannula device resulted in a similar rostro-caudal spread than with the five tract paradigm at both flow rates (6.2-8.6 mm spread for the 28-gauge cannula and 7.8 mm spread with the five tracts and discontinuous flow-rate). A lower rostro-caudal spread was observed with a single infusion using the 23-gauge needle and Hamilton syringe (5.0-6.2 mm spread).

When the total volume of vector distribution was compared it was surprisingly found that the single administration of 50 µL of vector using a 23-gauge delivery device was less than the five-tract delivery method. Even more surprising, the 28-gauge delivery device gave a greater volume of vector distribution than the five-tract method—more than twice the volume with the higher flow rate. This increase in volume was at least partially thought to result from reduced backflow of vector along the needle tract using this narrow bore delivery device.

Overall these observations were consistent with the vector spreading evenly from the tip of the device when a single infusion was performed with the 28-gauge cannula. Conversely, with the 5 tract delivery approach and to a less extent with the single infusion using the 23-gauge needle and syringe, the distribution of vector was more confined to the area directly around the needle tract. There was no evidence for damage to surrounding neuronal tissue or rupture of the blood-brain barrier as a result of the infusions in all groups. A 33-gauge plastic cannula was also evaluated but was considered too flexible to be used for routine surgery potentially contributing to the failure of the surgeon to place the cannula at the correct site within the putamen. The 28-gauge fused silica cannula resulted in a similar spread of vector using both flow rates (1 or 3 µL/min). The finer gauge 28-gauge cannula resulted in less scarring than the 23-gauge Hamilton needle. A similar number of cells (>90%) were doubly stained for β-galactosidase and for NeuN irrespective of the delivery paradigm, confirming neuronal targeting of the vector in all cases.

The local inflammatory response to infusion of EIAV-LacZ vector was assessed in this study by histological evaluation of inflammatory markers CD4 and CD8 (T-cells) and CD68 (activated microglia). Positive staining for each of the markers was observed in the vicinity of the needle tract for all of the methods of delivery and injection devices, however, there was very little vector-associated inflammatory response and no differences between the administration methods were observed. This result indicates that the there is no increased inflammatory response associated with vector delivery using a single infusion at a higher flow.

No overt toxicity or abnormal clinical signs to vector administration was observed in any of the study animals. Animals did not display any abnormal locomotor activity or behaviour and were observed to feed normally.

TABLE 1

Summary of vector distribution using different vector delivery parameters

| Delivery Parameters | Rostro-caudal spread of vector (mm) |
|---|---|
| 50 µL delivered through 5 tracts using a 23-gauge Hamilton syringe 1 µL/min | 7.8 and 7.8 |
| Single 50 µL infusion using a 23-gauge Hamilton syringe, 1 µL/min | 5.8 and 6.2 |
| Single 50 µL infusion using a 23-gauge Hamilton syringe, 3 µL/min | 5.0 |
| Single 50 µL infusion using a 28-gauge fused silica cannula, 1 µL/min | 8.6 and 6.2 |
| Single 50 µL infusion using a 28-gauge fused silica cannula, 3 µL/min | 7.0 and 6.2 |
| Single 100 µL infusion using a 28-gauge Hamilton syringe, 3 µL/min | |
| Single 100 µL infusion using a 28-gauge fused silica cannula, 3 µL/min | |

TABLE 2

Data from a single experiment showing the distribution volume.

| Injection Device | Injection volume/method | Injection Flow Rate | A-P distribution (mm) | Volume of distribution (mm³) |
|---|---|---|---|---|
| Stainless steel needle and glass syringe (23-gauge) | 50 µL vector delivered through 5 injection tracts with three deposits per tract | 1 µL/min | 7.8 | 35.1 |
| Stainless steel needle and glass syringe (23-gauge) | 50 µL, single infusion | 1 µL/min | 5.8 | 10.0 |
| | | 3 µL/min | 5.0 | 25.7 |
| Fused silica cannula (28-gauge) | 5 µL, single infusion | 1 µL/min | 8.6 | 60.2 |
| | | 3 µL/min | 7.0 | 91.7 |

Conclusion

Previously, small volumes of lentiviral vectors have been delivered to the brain via multiple deposits within each cannula tract using slow flow rates. Such a method is cumbersome and has not enabled dose escalation studies. A simplified continuous infusion paradigm that allows the administration of greater volumes of vector at a faster flow rate was considered to be more applicable to surgical employment in the treatment of various neurological conditions.

It was not known whether vectors as large as lentiviruses could be effectively distributed into the brain through a single infusion paradigm as these vectors are considerably larger that the AAV particles which have been examined previously in primate brain (Bankiewicz et al (2000) Exp. Neurol. 164: 2-14; Hadaczek et al (2006) Hum. Gene Ther 17:291-302 and Hadaczek et al (2009) Hum. Gene Ther 20:229-237). As the diameter of lentiviral vectors (around 100 nm) is larger than the extracellular space (38-64 nm), it is possible that lentiviral vector particles would not have been effectively driven through the extracellular space, which may be prohibitive for particles as large as the lentiviral vectors. It is, however, clear that lentiviral vectors such as EIAV vectors can be effectively driven through the putamen region using a continuous infusion method that is easily controlled and which provides a volume of transduction that is better than spotting the vector around the target region using multiple cannula placements.

Previous studies in rodents have reported that at low flow rates and during the CED process, vector can spread through the perivascular space, possibly driven by the pulsatile action of blood flow through the brain capillary network (Hadaczek et al (2004) Hum Gene Ther. 15:469-79). However, we have found little evidence of this phenomenon when the flow rate was maintained at a high level. Restricting this perivascular transport may reduce vector distribution to non-target areas.

There has been concern that some viral vectors may pose a risk of central inflammation and that infusing vectors, at a single flow rate, or through the process of CED may exacerbate an inflammatory response. It has been recently demonstrated that the AAV serotype-1 vectors, which have been examined as carriers of therapeutic genes, produced a robust humoral and cellular response when administered to the striatum and cortex of primates (Hadaczek et al (2009) Hum. Gene Ther 20:229-237). No evidence for an increased local imflammatory response has been observed with a single infusion of an EIAV-based vector using a 28-gauge cannula with administration flow rates of between 1 and 3 µL/min.

In conclusion, these studies indicate that therapeutic genes aimed at treating various neurological conditions may be safely administered by the EIAV vector to target brain regions using the simplified infusion paradigm and that a wide volume of target cells can be effectively transduced.

Methods and Materials

Animals

Six male and six female cynomolgus macaques were housed in single sex compatible groups during their acclimatisation period at constant temperature (22±2° C.) and humidity (45%-65%) under a 12 hour light/dark cycle (lights on 07:30) prior to vector administration. The animals were then singly housed following surgical administration of vector in individual stainless steel boxes of standard dimensions of 1.10 m² floor surface×1 m high. Air in the animal room was changed approximately 10 times per hour. Animals were fed Old World Monkey pellets (SDS DIETEX #808004) and had access to tap water ad libitum. Animals use and care was administered to the Directive 86/609/EEC European Convention for the Protection of Vertebrate Animals used for Experimental and Other Scientific Purposes and the Animals (Scientific Procedure) Act 86 for the United Kingdom.

Vector Administration

Animals were fasted prior to surgery and water prevented access to water for approximately 6 hours. The animals were administered atropine sulphate (0.04 mg/kg, i.m.), ketamine HCl (10 mg/kg, i.m.) and buprenorphine (0.01 mg/kg, i.m.) and then anaesthetised with propofol (3 mg/kg i.v.) 10 min later. Animals were also injected with amoxicillin (30 mg/kg, s.c.) 24 hours prior to surgery and then every 48 hours up to one week after the surgery. The animals were inturbated and maintained in anaesthesia with isoflurane inhalant anaesthetic delivered through a volume-regulated respirator. The ECG, $O_2$ saturation and heart rate was monitored and recorded. Body temperature was monitored throughout the surgery using a rectal thermometer. The animals were placed in a stereotaxic frame (Unim'ecanique, France) and vector administered into the putamen using the microinjector system (Kopf, USA) for administration of vector as single small deposits in the putamen using a 6.5 mm long 23-gauge stainless steel Hamilton needle attached to a 710 Hamilton syringe (Hamilton Bonaduz A G, Bonaduz, Switzerland). For the single putamen infusions, vector suspensions were infused using either 6.5 mm long 23-gauge stainless steel Hamilton needle and syringe, 6.5 mm long 28-gauge stainless steel Hamilton needle and syringe or 6.5 mm long fused silica injection cannula attached to a Hamilton syringe by a short piece of plastic tubing to minimise the dead volume (Plastics-1, Roanoke, Va., USA). After drilling a hole in the skull without damaging the dura mater, a ventriculographic cannula mounted on a glass syringe was introduced into the anterior horn of the lateral ventricle and a contrast medium (Omnipaque, Nycomed, Norway) injected. A stereotaxic atlas was used for precise adjustment before insertion into the skull (Martin & Bowden (1996) Neuroimage 4(2):119-150). Accurate position of the anterior commissura (AC) was be deduced from ventriculography which was then used to position both left and right putamen. The coordinates for placement of the infusion cannulas was AC—1 mm (directly centre of the motor area of the putamen). For multiple deposits within each putamen, vector was injected at 3 depths delivering 4 mL at the deepest deposit and then a further two deposits of 3 mL each delivered 1 mm above one another to deliver 10 mL per needle tract. The first of five Hamilton needle tracts was at the level of the anterior commissure (AC), i.e. AC 0 mm, the second injection: 2 mm caudal to the AC (AC—2 mm), third injection: 3 mm caudal to the AC (AC—3 mm), forth injection: 5 mm caudal to the AC (AC—5 mm), and fifth injection: 6 mm caudal to the AC (AC—6 mm) to distribute vector along the rostro-caudal length of the putamen. The Hamilton syringe and infusion catheter will be left in situ for an additional 2 minutes after each injection/infusion before being removed.

Vector was infused at a single flow rate of 0.5, 1 or 3 μL/min using an a programmable small infusion pump (UltraMicroPump III; World Precision Instruments, Sarasota, Fla., USA). Vector was administered bilaterally into the putamen in a total volume of 50 μL per hemisphere with each hemisphere receiving vector delivered by a different flow rate or cannula device. In one animal, TSSM formulation buffer was infused into the putamen, in one hemisphere using the 23-gauge Hamilton needle delivering buffer at 1 mL/min and in the other hemisphere the vector was delivered by a 28-gauge Hamilton needle at 1 mL/min. The TSSM-infused animal was used to assess the relative extend on neuronal damage and inflammation response to sterile formulation buffer alone, in the absence of viral vector. surgical records. Following surgery, the animals were closely observed and kept warm until they had regained the righting and swallowing reflexes before being returned to their cages. Buprenorphine analgesia was administered twice daily, for 3 days (0.02 mg/kg, i.m.) and body weights were recorded weekly after surgery.

Histology

Animals were necropsied 4 weeks after dosing and following an overnight fast through injection of ketamine (10 mg/kg) and then euthanasia using sodium pentobarbital anaesthesia (between 10-30 mg/kg, i.v.). Following collection of a blood sample for assessment of the immune response to the virus, the animals were exsanginated, perfused with heparinized phosphate buffered saline (0.9% w/v sodium chloride, USP containing approximately 25 U/mL heparin) followed by a solution of 4% buffered paraformaldehyde in phosphate buffered saline (PBS). The brains (with the dura removed) were carefully dissected and placed in fresh 4% paraformaldehyde overnight at 5±3° C. and then transferred to cold filtered 30% sucrose solution in PBS for between 2 and 4 days. The brains were then bisected down the midline into two hemispheres and each hemisphere snap frozen in cold isopentane (−40 to −50° C.) and stored at −80° C. before sectioning at forty micron (40 μm) thickness using a cryostat. Brain sections containing the putamen region were collected in pots containing 5 sections equating a distance of two hundred microns (200 μm) travel in the rostro-caudal axis of brain hemisphere. Free-floating brain sections were stained with anti-β-galactosidase monocloncal antibodies. Secondary and tertiary antibodies were obtained from the Vectastain anti mouse ABC kit (#PK-6102) and the methodology was as per kit instructions. DAB visualisation was achieved using a DAB peroxidise substrate kit (catalogue number SK-4100). Sections were then mounted on glass microscope slides. Alternative brain hemisphere sections were stained with anti-GFAP antibody (Chemicon #MAB3402) at a concentration of 1:200. Selected sections were also stained using H&E and the sections analysed microscopically to assess levels of cell infiltrates and changes in tissue morphology. Selected sections in the region of vector infusion were also stained for the immunological markers CD8, CD4 and CD68 after removing non-specific staining with 10% hydrogen peroxide followed by an overnight incubation in 10% serum with 0.5% triton X-100. Primary antibodies (IgG negative control, no primary negative control, mouse anti human CD4, CD8 and CD68) were applied for two hours only. After three 5 minute washes in PBS+0.02% Tween 20 the anti-mouse vector elite ABC kit was used with three 5 minute washes in between each step. A DAB peroxidase kit was then used for visualisation.

The volume of vector distribution was calculated by measuring the area of positive β-galactosidase staining in serial brain sections throughout the injected putamen and applying standard stereology methods (using Cavalieri's principle) to estimate total volume coverage.

Example 2

Comparing Efficacy of a Lentiviral Vector for Parkinson's Disease Following Administration to the Motor Putamen of Parkinson's Disease Patients Using a) Conventional Delivery and b) Delivery Using a Reduced Number of Injection Sites with a Narrower Gauge Device and a High Flow-rate A phase I/II clinical trial is ongoing to evaluate the safety and efficacy of a lentiviral vector based treatment for Parkinson's disease, called ProSavin®. ProSavin® is an EIAV lentiviral vector that contains three genes which encode for enzymes in the dopamine biosynthesis pathway. As part of the trial the therapeutic potential of ProSavin® to correct symptoms of Parkinson's disease was evaluated using 1) the conventional method of administration and 2) a continuous method of infusion. The conventional method involved injection of a total volume of 1254 of vector administered to each putamen through 5 needle tracts using a Hamilton syringe and 23-gauge needle and an administration rate of 1 μL/min. A total of 25 μL of vector was administered along each injection tract with 5 deposits of 5 μL of vector distributed along the tract. In the continuous method of delivery the same total volume of vector was administered (1254) using a Hamilton syringe and a narrower 28-gauge needle. Three injections were performed into each putamen and a continuous infusion of vector was made at each injection site using an increased administration rate of 3 µL/min. The volumes of vector delivered were 42 µL, 42 µL and 43 µL at the three injection sites. The surgical time for vector administration using the infusion method was almost half of that compared to the conventional method.

The surgical procedures were safe and well tolerated in all patients with both administration methods. There were no serious adverse events reported in any patients relating to either ProSavin® or the two administration methods.

The primary efficacy endpoint of the study was improvement in the motor part (part III) of the Unified Parkinson's Disease Rating Scale (UPDRS) at 6 months post treatment, compared with baseline scores. A summary of improvements in motor function to date, is shown in Table 3 (motor function is assessed according to the Unified Parkinson's Disease Rating Scale [UPDRS] in patients' "OFF" state, i.e. after withdrawal of Parkinson's disease medication). In the group of patients receiving ProSavin® using the conventional, discontinuous, 5-deposit/tract method an improvement of 34% in UPDRS part III scores was observed at 6 months. Interestingly, patients that received the same total volume of vector using the continuous infusion method showed a greater improvement in UPDRS part III scores, reaching a 43% improvement at 6 months post treatment.

entering the putamen. For the conventional method of administration ProSavin® was loaded into a Hamilton syringe attached to a 23 gauge point two style bevelled non coring needle, 150 mm in length. For the continuous infusion method ProSavin® was loaded into a Hamilton syringe attached to a 28-gauge needle of the same length. The needle was lowered into the brain through the guide tube and penetrated the motor putamen The guide tube was then withdrawn approximately 10 mm prior to infusion of ProSavin®. A new guide tube, Hamilton syringe and needle were used for each hemisphere of the brain.

For the conventional method of administration 25 µL of ProSavin® was administered to each of five separate tracts in both brain hemispheres. Each tract received five deposits of 5 µL of ProSavin®. The deepest deposit was administered first, the needle was then withdrawn by 1 mm and a second deposit of 5 µL was administered. This was repeated until all five deposits had been made. Administration was performed manually in each of the injection tracts at a rate of 1 µL per minute (0.5 µL will be injected, followed by a 30 second pause before the next 0.5 µL is injected and so on) until 5 µL was injected into the five deposits along each tract. The needle was left in situ for one minute on completion of all five deposits on a single tract.

For the continuous infusion method ProSavin® was administered into three injection tracts per hemisphere. Volumes of 42 µL, 42 µL and 43 µL of ProSavin® were administered using continuous infusion at a constant delivery rate of

TABLE 3

| Cohort[2] | Dose | Administration method | 3 months (UPDRS) | 6 months. (UPDRS) | 1 year (UPDRS) | 2 years (UPDRS) |
| --- | --- | --- | --- | --- | --- | --- |
| 1, n = 3 | 1x | Conventional | Mean 27% Max. up to 30% | Mean 30% Max. up to 50% | Mean 29% Max. up to 44% | Mean 20% Max. up to 30% |
| 2, n = 3 | 2x | Conventional | Mean 28% Max. up to 53% | Mean 34% Max. up to 53% | Mean 29% Max. up to 56% | — |
| 2b, n = 3 | 2x | Continuous Infusion | Mean 26% Max. up to 52% | Mean 43% Max. up to 61% | — | — |

In addition patients showed an average improvement of 26% in UPDRS part III "ON" score at 6 months. Patient diary data showed an increase in functional improvement in the time oral L dopa was effective without troubling dyskinesias of 3.2 hours and a decrease in the time that oral L dopa was ineffective of 4.1 hours.

The results indicate that the continuous infusion method provides increased efficacy in Parkinson's patients compared to the discontinuous, 5-deposit/tract method previously used. The reason for this may be due to an improved distribution of the ProSavin® vector in the injected putamen, although it is not possible to assess this in living patients. Furthermore, the surgical time for vector administration using the continuous infusion method was almost half of that compared to the conventional method.

Methods and Materials

All patients were injected with ProSavin® intrastriatally under general anaesthesia using bilateral stereotaxic injections. A cranial MRI scan was performed prior to the administration to provide precise injection coordinates for targeting the sensorimotor putamen region of the putamen.

For each injection a guide tube of 130 mm in length with a bore diameter of 1.2 mm was inserted into the correct position within the brain, using the MRI-derived coordinates, without 3 µL/min. The flow rate was controlled by the use of a pump rather than the manual system described above for the conventional method.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, virology, neurology or related fields are intended to be within the scope of the following claims.

The invention claimed is:

1. A method for delivering a lentiviral vector to the putamen of a primate subject, wherein the method comprises directly administering to the putamen of the primate subject via continuous infusion, using a cannula with a bore equivalent to or narrower than 28 gauge, a composition comprising a lentiviral vector, wherein the composition is delivered at a flow rate of at least 2 µL/min.

2. The method according to claim 1, wherein a constant flow rate is maintained during infusion of the lentiviral vector.

3. The method according to claim 1, wherein the flow rate is increased during infusion of the lentiviral vector.

4. The method according to claim 1, wherein the lentiviral vector is an equine infectious anaemia virus (EIAV) vector.

5. The method according to claim 4, wherein the EIAV vector-comprises nucleotide sequences encoding Tyrosine Hydroxylase, GTP-cyclohydrolase I and Aromatic Amino Acid Dopa Decarboxylase.

6. The method according to claim 1, wherein the lentiviral vector is delivered via a single tract per hemisphere.

7. The method according to claim 6, wherein the infusion has a volume of about 50 μL per tract.

8. The method according to claim 1, wherein the flow rate at which the lentiviral vector is delivered is 2-4 μL/min.

9. The method according to claim 1, wherein the flow rate at which the lentiviral vector is delivered is about 3 μL/min.

10. The method according to claim 1, wherein the lentiviral vector is delivered via between one and six tracts per hemisphere.

11. The method according to claim 1, wherein 40-200 μL of the composition is delivered per tract.

12. The method according to claim 1, wherein 10-600 μL of the composition is delivered per tract.

13. The method according to claim 1, wherein the lentiviral vector is delivered via one, two, or three tracts per hemisphere.

* * * * *